(12) United States Patent
Sohrab (10) Patent No.: US 6,793,632 B2
(45) Date of Patent: Sep. 21, 2004

(54) PERCUTANEOUS BIOLOGICAL FLUID CONSTITUENT SAMPLING AND MEASUREMENT DEVICES AND METHODS

(75) Inventor: Borzu Sohrab, Los Altos, CA (US)

(73) Assignee: LifeScan, Inc., Milpitas, CA (US)

( * ) Notice: Subject to any disclaimer, the term of this patent is extended or adjusted under 35 U.S.C. 154(b) by 213 days.

(21) Appl. No.: 09/878,742

(22) Filed: Jun. 12, 2001

(65) Prior Publication Data

US 2002/0188221 A1 Dec. 12, 2002

(51) Int. Cl.$^7$ .................................................. A61B 5/00
(52) U.S. Cl. ...................... 600/573; 600/347; 600/584; 422/68.1; 422/82.01; 436/149
(58) Field of Search ................... 600/573, 584, 600/575, 576, 345–358, 365, 366, 372, 373, 393; 606/185, 186; 422/68.1, 82.01–82.03; 435/14; 436/149, 150; 204/400, 403.01

(56) References Cited

U.S. PATENT DOCUMENTS

| | | |
|---|---|---|
| 5,161,532 A | 11/1992 | Joseph |
| 5,582,184 A | 12/1996 | Erickson et al. |
| 5,746,217 A | 5/1998 | Erickson et al. |
| 5,879,310 A | 3/1999 | Sopp et al. |
| 5,879,367 A | 3/1999 | Latterell et al. |
| 5,942,102 A | 8/1999 | Hodges et al. |
| 6,080,116 A | 6/2000 | Erickson et al. |
| 6,083,196 A | 7/2000 | Trautman et al. |
| 6,091,975 A | 7/2000 | Daddona et al. |
| 6,162,611 A | 12/2000 | Heller et al. |
| 6,438,414 B1 * | 8/2002 | Conn et al. .......... 604/20 |
| 2002/0133129 A1 * | 9/2002 | Arias et al. .......... 604/272 |
| 2002/0168290 A1 * | 11/2002 | Yuzhakov et al. ...... 422/56 |
| 2002/0185384 A1 * | 12/2002 | Leong et al. .......... 205/775 |
| 2002/0187556 A1 * | 12/2002 | Shartle et al. ......... 436/149 |
| 2002/0188184 A1 * | 12/2002 | Kiser et al. ........... 600/345 |
| 2002/0188185 A1 * | 12/2002 | Sohrab ................. 600/347 |
| 2003/0055326 A1 * | 3/2003 | Sohrab ................. 600/347 |

FOREIGN PATENT DOCUMENTS

| | | |
|---|---|---|
| WO | WO 97/00441 | 1/1997 |
| WO | WO 97/42888 | 11/1997 |
| WO | WO 98/00193 | 1/1998 |
| WO | WO 908/34541 | 8/1998 |
| WO | WO 99/13336 | 3/1999 |
| WO | WO 99/27852 | 6/1999 |
| WO | WO 99/64580 | 12/1999 |
| WO | WO 00/35530 | 6/2000 |
| WO | WO 00/45708 | 8/2000 |
| WO | WO 00/57177 | 9/2000 |
| WO | WO 00/74763 | 12/2000 |
| WO | WO 00/74765 | 12/2000 |

* cited by examiner

*Primary Examiner*—Charles A. Marmor, II
(74) *Attorney, Agent, or Firm*—Carol M. LaSalle; Bozicevic, Field & Francis, LLP (57) ABSTRACT

A device for sampling at least one biological fluid constituent and measuring at least one target constituent within the biological fluid. The device has at least one micro-needle having an open distal end used to penetrate the skin to a depth where pain and bleeding are minimized. The device further includes a hydrophilic gel within the micro-needle for sampling the biological fluid constituents and an electrochemical cell for measuring the concentration of targeted constituents within the sampled biological fluid constituents. In certain embodiments, the electrochemical cell is integrated within the micro-needle whereby the steps of sampling and measuring are performed completely in-situ. In other embodiments, the electrochemical cell is located external to the micro-needle at its proximal end. Constituent sampling and measurement systems, methods and kits are also provided.

12 Claims, 3 Drawing Sheets

PERCUTANEOUS BIOLOGICAL FLUID CONSTITUENT SAMPLING AND MEASUREMENT DEVICES AND METHODS

FIELD OF THE INVENTION

This invention is related to percutaneous biological fluid sampling and analyte measurement, and more particularly to constituent transfer mediums to facilitate sampling of biological fluid.

BACKGROUND OF THE INVENTION

The detection of analytes in biological fluids is of ever increasing importance. Analyte detection assays find use in a variety of applications, including clinical laboratory testing, home testing, etc., where the results of such testing play a prominent role in the diagnosis and management of a variety of disease conditions. Common analytes of interest include glucose, e.g., for diabetes management, cholesterol, and the like.

A common technique for collecting a sample of blood for analyte determination is to pierce the skin at least into the subcutaneous layer to access the underlining blood vessels in order to produce localized bleeding on the body surface. The accessed blood is then collected into a small tube for delivery and analyzed by testing equipment, often in the form of a hand-held instrument having a reagent test strip onto which the blood sample is placed. The fingertip is the most frequently used site for this method of blood collection due to the large number of small blood vessels located therein. This method has the significant disadvantage of being very painful because subcutaneous tissue of the fingertip has a large concentration of nerve endings. It is not uncommon for patients who require frequent monitoring of an analyte to avoid having their blood sampled. With diabetics, for example, the failure to frequently measure their glucose level on a prescribed basis results in a lack of information necessary to properly control the level of glucose. Uncontrolled glucose levels can be very dangerous and even life-threatening. This technique of blood sampling also runs the risk of infection and the transmission of disease to the patient, particularly when done on a high-frequency basis. The problems with this technique are exacerbated by the fact that there is a limited amount of skin surface that can be used for the frequent sampling of blood.

To overcome the disadvantages of the above technique and others that are associated with a high degree of pain, certain analyte detection protocols and devices have been developed that use micro-needles or analogous structures to access the interstitial fluid within the skin. The micro-needles are penetrated into the skin to a depth less than the subcutaneous layer so as to minimize the pain felt by the patient. The interstitial fluid is then sampled and tested to determine the concentration of the target constituent. The concentration of a constituent within the interstitial fluid is representative of the concentration of that constituent in other bodily fluids, such as blood.

Conventional micro-needle sampling systems have a drawback in that, because the interstitial fluid inside the human body is at a negative pressure of about 6 mm/Hg, some kind of mechanical or vacuum means is often used in conjunction with the micro-piercing members.

For example, International Patent Application WO 99/27852 discloses the use of vacuum pressure and/or heat to increase the availability of interstitial fluid at the area of skin in which the vacuum or heat is applied. The vacuum pressure causes the portion of skin in the vicinity of the vacuum to become stretched and engorged with interstitial fluid, facilitating the extraction of fluid upon entry into the skin. Another method is disclosed wherein a localized heating element is positioned above the skin, causing interstitial fluid to flow more rapidly at that location, thereby allowing more interstitial fluid to be collected per given unit to time.

Still other detection devices have been developed which avoid penetration of the skin altogether. Instead the outermost layer of skin, called the stratum corneum, is "disrupted" by a more passive means to provide access to or extraction of biological fluid within the skin. Such means includes the use of oscillation energy, the application of chemical reagents to the skin surface, etc. For example, International Patent Application WO 98/34541 discloses the use of an oscillation concentrator, such as a needle or wire, which is positioned at a distance from the skin surface and caused to vibrate by means of an electro-mechanical transducer. The needle is immersed in a receptacle containing a liquid medium placed in contact with the skin. The mechanical vibration of the needle is transferred to the liquid, creating hydrodynamic stress on the skin surface sufficient to disrupt the cellular structure of the stratum corneum. International Patent Applications WO 97/42888 and WO 98/00193 also disclose methods of interstitial fluid detection using ultrasonic vibration.

Thus, despite the work that has already been done in the area of analyte testing, there is a continued interest in the identification of new analyte detection methods that more readily meet the needs of the relevant market. Of particular interest would be the development of a minimally invasive analyte detection system that is practical, manufacturable, accurate and easy to use, as well as safe and efficacious.

Relevant Literature

U.S. Patents of interest include: U.S. Pat. Nos. 5,582,184, 5,746,217, 5,820,570, 5,942,102, 6,091,975 and 6,162,611. Other patent documents and publications of interest include: WO 97/00441, WO 97/42888, WO 98/00193 WO 98/34541, WO 99/13336, WO 99/27852, WO 99/64580, WO 00/35530, WO 00/57177 and WO 00/74765A1.

SUMMARY OF THE INVENTION

Percutaneous biological fluid sampling and analyte measurement systems and devices, as well as methods for using the same are provided by the subject invention. A feature of the subject devices is the presence of a constituent transfer medium that samples and transfers at least the target constituent(s) of biological fluid accessed within the skin to an electrochemical cell for measurement of the targeted constituent(s) within the fluid sample. The present invention finds use in accessing biological fluids such as blood and interstitial fluid, and in the detection and measurement of various analytes, e.g., glucose, cholesterol, electrolytes, pharmaceuticals, or illicit drugs, and the like, which are present in the accessed biological fluid. The present invention is especially well-suited for the sampling and measurement of interstitial fluid constituents such as glucose.

In general, the subject sampling and measurement devices include an elongated skin-piercing or skin-penetrating means to provide access to the biological fluid, at least one sampling means in the form of a constituent transfer medium, and a measuring means in the form of an electrochemical measurement cell in fluid communication with the constituent transfer medium.

The skin-penetrating means includes at least one micro-needle defining a substantially annular bore or channel through at least a portion of the interior of the micro-needle structure and having an access opening at a distal end through which one or more biological fluid constituents enter into the device. In many embodiments, the skin-piercing means comprises an array of such micro-needles.

The electrochemical measurement cell comprises spaced-apart working and reference electrodes positioned within and/or further defining the micro-needle structure. The area between the electrodes is defined as the reaction zone in which the actual measurement of analyte concentration takes place. In certain embodiments, the electrode pair are co-axially positioned and concentrically-spaced from each other, wherein at least the outer electrode has a hollow, cylindrical configuration and, at least in part, defines the micro-needle structure. The inner electrode is positioned within the cylindrical wall of the outer electrode and may also have a cylindrical configuration, either as hollow cylinder filled with a center core material or as a solid cylinder. In other embodiments, the electrochemical cell defines the proximal end of the micro-needle structure in the form of two parallel-spaced planes positioned substantially transverse to the longitudinal axis of the micro-needle.

In operation, one of the electrodes of the electrochemical cell is used as the reference electrode by which an input reference signal is provided to the sensor from a signal generating means. The other electrode operates as a working electrode that provides an output signal from the sensor to a signal receiving means. Preferably, the reference electrode is located at the bottom and the working electrode is located at the top of the device. This output signal represents the concentration of the target analyte in accessed biological fluid.

A redox reagent system or material may be used within the electrochemical cell to facilitate targeting the analyte(s) of interest. The particular redox reagent material used is selected based on the analyte targeted for measurement.

The constituent transfer medium of the sampling means occupies the area between the two electrodes, referred to as the reaction zone, and at least a portion of each micro-needle channel. The constituent transfer medium is made of a hydrogel or gel material or matrix that is hydrophilic and has an affinity for ionic and anionic particles within biological fluid. Optionally, the gel matrix may be configured to transfer only particles having a molecular weight less than a specified weight. The gel acts to transfer at least the targeted biological fluid constituent(s) present at the access opening of a micro-needle into the reaction zone. In other words, the targeted constituent(s) migrates through the gel matrix until equilibrium is reached between the concentration of the constituent(s)within the tissue and the concentration of the constituent(s) within the gel matrix. As compared to a hollow micro-needle which relies solely on capillary force that it exerts on the biological fluid as a means to transfer the biological fluid to the electrochemical cell, the subject constituent transfer medium may be configured (i.e., presented in a fully saturated state) to eliminate the transfer of water and other fluids contained within the accessed biological fluid, while transferring only constituents of the biological fluid. It is the configuration of the electrochemical cell that selects the targeted constituent(s) from the remaining constituents for testing.

The gel matrix of the present invention is characterized by a concentration gradient that changes in accordance with a first order system. This allows calculation of ionic and non-ionic element concentrations by means of the exponential characteristics of the first order system.

The subject sensor devices may function as a part of an analyte sensing system that includes a means for controlling the sensor device. Specifically, a control unit is provided in which the control means is electrically coupled with the sensor device and functions to generate and send input signals to the electrochemical cell and to receive output signals from the cell. These functions, among others, are performed by a software algorithm programmed within the control unit that automatically calculates and determines the concentration of the target analyte in the biological sample upon receipt of an output signal from the electrochemical cell.

An exemplary method of the subject invention involves using at least one subject sensor device comprising one or more hollow micro-needles having an open distal end defining a constituent transfer pathway to an integrally-coupled electrochemical cell. A hydrophilic gel material fills the interior of the micro-needle and the electrochemical cell. The micro-needle is inserted into the skin to a selected depth, preferably to a depth that avoids contacting nerve endings and blood vessels. Next, the at least the targeted constituent(s) of the biological fluid present at the open distal end of the micro-needle is wicked into the gel material and transferred into the reaction zone of the electrochemical cell. An electrochemical measurement is then made between the working and reference electrodes that provides an electrical signal that is representative of the concentration the constituent in the sample. The concentration of the constituent in the patient's blood is then derived from the obtained electrical signal. A numerical value representing this concentration may then be displayed on a display unit. A software algorithm that is part of the device, e.g., programmed into a control unit present in the device, may be employed to determine the signal levels transmitted by the control unit to the cell and for deriving the concentration level of the target analyte.

The subject devices, systems and methods find use in analyte concentration measurement of a variety of analytes and are particularly suited for use in the measurement of glucose concentration in interstitial fluid.

BRIEF DESCRIPTION OF THE DRAWINGS

FIG. 1 includes FIGS. 1A, 1B, 1C and 1D wherein

FIG. 2 includes FIGS. 2A and 2B wherein

DETAILED DESCRIPTION OF THE INVENTION

Percutaneous biological fluid, e.g., interstitial fluid, sampling and analyte measurement sensor devices and systems, as well as methods for using the same, are provided. The present invention finds use in the sampling of constituents found in biological fluids such as blood and interstitial fluid, and in the detection and measurement of a variety of different analytes, e.g., glucose, cholesterol, electrolytes, pharmaceuticals, illicit drugs, and the like.

In general, the subject devices include a skin-piercing means, a biological fluid constituent sampling means in the form of a constituent transfer medium, and a constituent concentration measuring means in the form of an electrochemical cell in fluid communication with the constituent transfer medium. Preferably these components are integrated into a single structure.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a test strip" includes a plurality of such test strips and reference to "the processor" includes reference to one or more processors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

The Skin-penetration Means

The skin-penetration means comprises at least one micro-piercing member, preferably in the form of a micro-needle, used to penetrate the skin to a depth where pain and bleeding are minimized, and preferably non-existent. Thus, it is preferable that the micro-needle penetrates above the level where nerves are present. As such, target skin layers into which the subject piercing members may extend include the dermis, epidermis and the stratum corneum (i.e., the outermost layer of the epidermis).

The micro-needle defines a substantially annular bore or channel through the interior of a narrow, elongated structure having a distal access opening through which biological fluid constituents may enter into the micro-needle. In certain embodiments of the sensor devices of the present invention, the skin-piercing means comprises an array of such micro-needles.

The subject micro-needles are configured to be mechanically stable and strong enough to penetrate the stratum corneum without breaking or flexing. Preferably, they are made of a biocompatible material so as not to cause irritation to the skin or an undesirable tissue response. Although the sensor devices may be disposable, for reusable embodiments, it is preferable that the material of the micro-needles and/or micro-needle arrays is able to withstand sterilization cycles.

The micro-needles and/or the array of micro-needles may be formed of or coated with an insulating material, such as a ceramic, glass, silica, polymer, plastics and the like. Examples of polymers are polyacrylates, epoxies, polyesters polyetheretherketone, liquid crystalline polyesters, or their composites. Examples of ceramics are aluminum oxide, silicon carbide and zirconium oxide. Suitable metallic materials include stainless steel, titanium, precious metals or alloys thereof and the like.

Figure 1A:
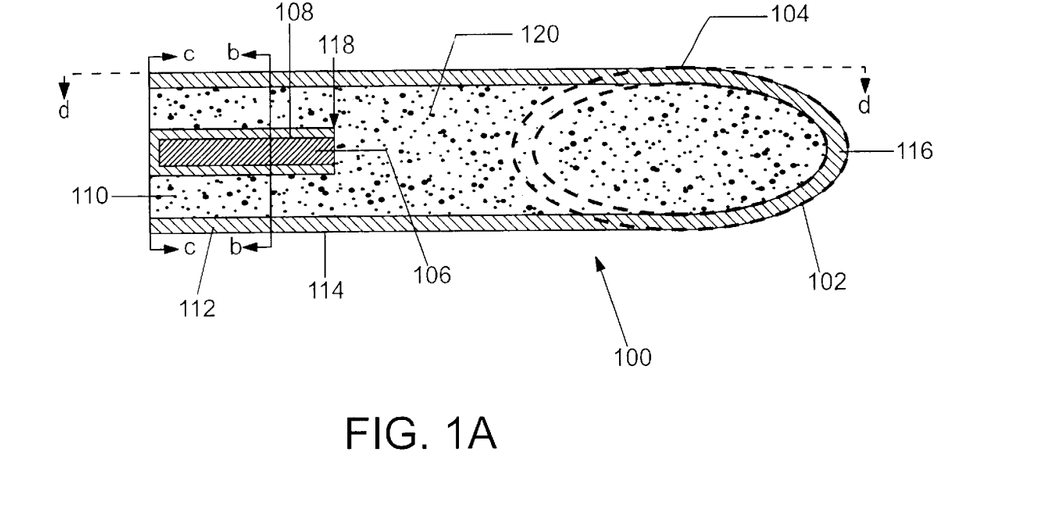
FIG. 1A is a cut-away view of a length of an embodiment of the micro-needle of the present invention.

The general configuration of exemplary micro-needles of the present invention will now be described with reference to FIGS. 1 and 2. FIGS. 1A and 2A illustrate micro-needles 100 and 200, respectively, having a configuration that is substantially straight along the longitudinal axis and has a substantially circular cross-section. However, any suitable cross-sectional configuration may be employed including, but not limited to other annular shapes such as elliptical or oblong, or polygonal configurations, such as square and rectangular. The outer diameter of a micro-needle at its thickest point is between about 200 $\mu$m to 300 $\mu$m, and typically does not exceed about 350 $\mu$m. In certain embodiments the outer diameter is typically about 250 $\mu$m.

An important aspect of the present invention is to eliminate or at least greatly minimize the pain and bleeding suffered by a patient during the sampling process. Accordingly, the penetration lengths and diameters of the micro-needles must be within certain ranges to accomplish this goal. Of course, those values will vary depending on the type of biological fluid (e.g., interstitial fluid, blood or both) desired for sampling and the thickness of the skin layers of the particular patient being tested.

The skin includes three distinct layers, a top layer called the epidermis, a middle layer called the dermis and a bottom layer called the subcutaneous layer. The epidermis is about 60 to 120 $\mu$m (microns) thick and comprises four distinct layers: a 10 to 20 $\mu$m outer layer, called the stratum corneum, followed by the stratum granulosum, stratum malpighii and stratum germinativum. The stratum corneum contains cells filled with bundles of cross-linked keratin and keratohyalin surrounded by an extracellular matrix of lipids. The inner three layers are collectively referred to as the viable epidermis and have a total thickness in the range of about 50 to 100 $\mu$m. The viable epidermis is responsible for diffusing metabolites to and from the dermis. The epidermis contains no blood cells or nerve endings. The dermis is much thicker than the epidermis, having a thickness in the range from about 2,000 to 3,000 $\mu$m. The dermal layer generally consists of a dense bed of connective tissue, including collagen fibers, and interstitial fluid dispersed throughout these fibers. Below the dermal layer is the subcutaneous tissue that contains the blood capillaries and the majority of nerve endings within the skin.

Thus, the micro-needles of the present invention preferably have penetration lengths that extend no deeper than the dermis layer when fully penetrated into the skin in order to minimize pain, however, they may be longer if necessary for the particular sampling application at hand. The length-to-diameter aspect ratio of the micro-needle is another factor to consider in determining an optimal length for the subject micro-needles. In order to effectively and atraumatically penetrate the skin, the length of the micro-needle is generally at least about 5 times greater than the diameter of the micro-needle, but may be more or less. The minimum micro-needle diameter is dependent upon the necessary spacing between the electrodes and the diameters of the other components of the electrochemical cell.

Thus, the subject micro-needles generally have a length in the range from about 500 to 4,000 $\mu$m, typically between about 600 to 3,000 $\mu$m, and more typically between about 1,000 to 2,000 $\mu$m; however, these lengths will vary from patient to patient depending on the thickness of the skin layers of the particular patient being tested. While the micro-needles may have lengths that are longer than the depth of the target skin layer, the micro-needle may be penetrated into the skin at depth (referred to as the penetration length) that is less than the length of the micro-needle structure. Thus, in order to minimize pain to the patient, the micro-needles preferably have a penetration length in the range from about 50 to 4,000 $\mu$m, and more typically from about 100 to 3,000 $\mu$m. For example, for sampling applications that require penetration only into the epidermis layer, the penetration length of the micro-needle is typically between about 50 to 120 $\mu$m. For sampling applications which require penetration into but no deeper than the dermis layer, the penetration length of the micro-needle is typically from about 2,000 to 3,000 $\mu$m.

Figure 1B:
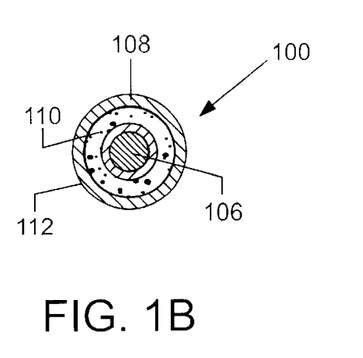
FIG. 1B is a cross-sectional view of the micro-needle of FIG. 1A along the arrows b—b.
Figure 1C:
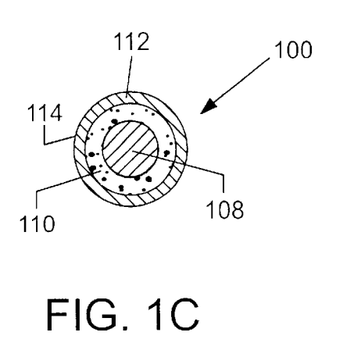
FIG. 1C is a cross-sectional view of the micro-needle of FIG. 1A along the arrows c—c and FIG. 1D is a top view of the micro-needle of FIG. 1A along the arrows d—d.
Figure 1D:
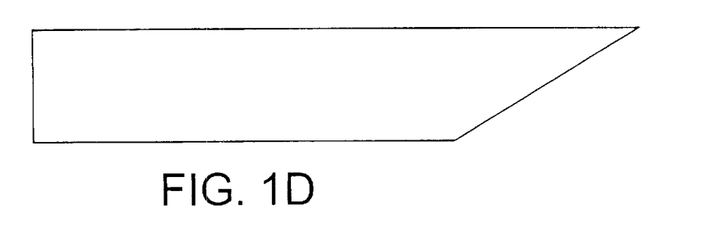

Micro-needles 100 and 200 terminate at distal ends 104 and 204, respectively, in preferably sharp tips 102 and 202, respectively, having a beveled or sliced configuration, as shown in FIG. 1D, to more easily penetrate the skin. However, tips 102 and 202 may have other suitable configurations such as one that is not tapered and defines an edge that lies in a plane perpendicular to the longitudinal axis of the micro-needle (not shown).

Any suitable number of micro-needles, in the form of an array, may be employed by the present invention. The number of micro-needles employed will depend upon various factors including the agent being detected, the body surface location into which the micro-needles are inserted, the sample site, the fluid volume and the like. The micro-needle array may comprise micro-needles having varying shapes, lengths, widths and tip configurations.

The Electrochemical Cell

The electrochemical cell of the present invention comprises an electrode arrangement of a working electrode and a reference electrode that provides an input reference signal to the sampled biological fluid constituent(s) and an output signal representing the concentration of the target constituent(s) or analyte(s) in the sampled fluid. The two electrodes are in a spaced-apart relationship such that a surface of one electrode faces a surface of the other electrode. The space between the two electrodes defines a reaction zone into which sampled constituent is transferred and is tested for the concentration of a targeted analyte.

Various types of electrochemical systems and methods commonly known in the art of analyte detection and measurement may be employed by the present invention, including systems that are amperometric (i.e., measure current), coulometric (i.e., measure electrical charge) or potentiometric (i.e., measure voltage). Examples of these types of electrochemical measurement systems are further described in U.S. Pat. Nos.: 4,224,125; 4,545,382; and 5,266,179; as well as WO 97/18465 and WO 99/49307; the disclosures of which are herein incorporated by reference.

Figure 2A:
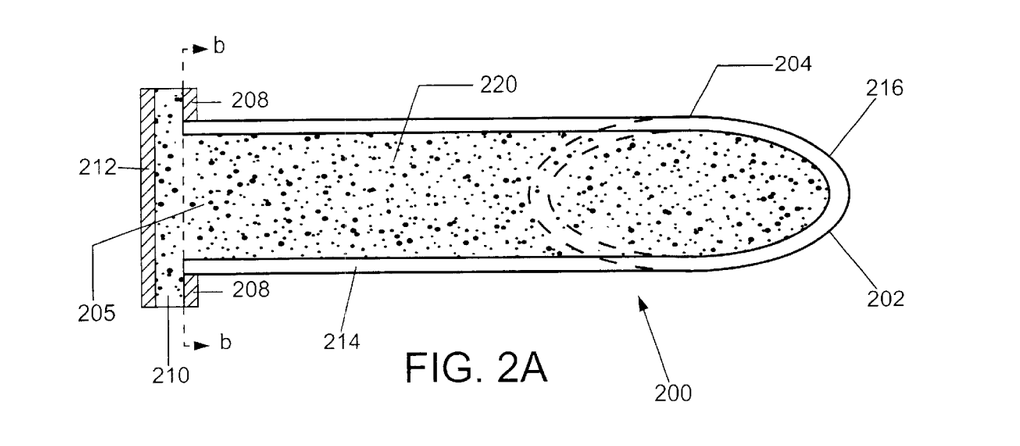
FIG. 2A is a cut-away view of a length of another embodiment of the micro-needle of the present invention and FIG. 2B is a cross-sectional view of the micro-needle of FIG. 2A taken along the arrows b—b.
Figure 2B:
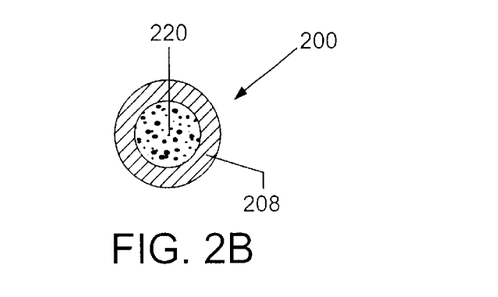

FIGS. 1 and 2 illustrate two exemplary embodiments of the electrochemical cell of the present invention. In particular, FIGS. 1A–C show an electrochemical cell embodiment having two co-axially aligned, concentrically-spaced electrodes fully housed within the micro-needle. FIGS. 2A and B show an electrochemical cell embodiment having two substantially planar electrodes parallely-spaced at a proximal end of the micro-needle.

Turning now to the embodiment of FIGS. 1A–C, micro-needle 100 includes an electrochemical cell that provides an electrical signal or signals representative of the concentration of the analyte being measured in a sampled biological fluid constituent. The electrochemical cell comprises various components or layers arranged concentrically with respect to each other. More specifically, this concentric arrangement may also be described as circumferential or co-axial.

Viewed longitudinally in FIG. 1A and in cross-section in FIG. 1B, micro-needle 100 includes, a solid wire core 106 and an outer plating 114. The solid wire core 106 provides rigidity to the micro-needle structure and may be part of the adjacent electrode. The outer plating 114 may be made of stainless steel or the like. Between wire core 106 and outer plating 114 resides the subject electrochemical cell, which includes a first or inner electrode 108, a second or outer electrode 112 and a reaction zone 110 therebetween. Second electrode 112 and outer plating 114 extend to define edge 116 and tip 102 of micro-needle 100.

As shown in the proximal end view of FIG. 1C taken along arrows c—c of FIG. 1A, first or inner electrode 108 is shown covering the proximal end of solid wire core 106; however, the proximal end may be exposed. First electrode 108 and solid wire core 106, extend evenly to a point 118 (proximal to distal end 104) wherein these two layers have distal edges that are flush with each other. A second electrode 112 and outer plating 114, which extends to a distal opening at distal edge 116, as viewed in FIG. 1A, define a lumen portion 120 having a lumenal wall.

The open or hollow space within micro-needle 100 defined by lumen 120 and reaction zone 110 is filled with a constituent transfer medium, here a hydrophilic gel material, as discussed above. The gel acts to absorb and transfer constituents of biological fluid present at tip 102 into lumen 120 and then into reaction zone 110.

Suitable dimensions for the various components of the electrochemical cell of FIG. 1 are as follows. Typically, the length of outer electrode 112 may be substantially same as the penetration depth of the micro-needle, and thus is generally not greater than about 4,000 $\mu$m or less depending on the desired length of penetration. More typically, the length of the outer electrode is between about 1,000 $\mu$m to 3,000 $\mu$m, and preferably about 2,000 $\mu$m. The inner electrode may have the same length as the outer electrode but is preferably shorter. The length of the inner electrode is generally about 20% shorter than the outer electrode and is generally not greater than about 3,200 $\mu$m or less, and is typically between about 800 to 2,400 $\mu$m, and is more typically about 1,600 $\mu$m.

Solid wire core 106 has a diameter in the general range from about 80 to 100 μm, and typically does not exceed about 120 μm. In certain embodiments the diameter is typically about 90 μm. First electrode 108 has a cylindrical configuration (although other configurations are possible) having a thickness in the general range from about 70 to 200 Angstroms, and typically does not exceed about 300 Angstroms. Thus, as first electrode is formed around core 106, it has an outside diameter that is slightly greater than that of core 106. Second electrode 112 also has a cylindrical configuration (although other configurations are possible) having a thickness in the general range from about 70 to 200 Angstroms, and typically does not exceed about 300 Angstroms. The reaction zone or spacing between the two electrodes also has a cylindrical configuration (although other configurations are possible) having a thickness in the general range from about 50 to 80 μm, and typically does not exceed about 200 μm. The thin outer tube 114 upon which the second electrode 112 is electroplated has a thickness in the general range from about 12 to 20 μm, and typically does not exceed 25 μm. Therefore, the total outside diameter of micro-needle 100 is generally no less than about 200 μm, and typically in the range from about 250 to 300 μm, and typically does not exceed about 350 μm. Lumen 120 has a volume generally in the range from about 20 to 140 nL, and typically does not exceed about 250 nL.

Referring now to the embodiment of FIGS. 2A and B, there is shown a micro-needle 200 having a tubular configuration defined by outer plating 214 and lumen 220. Lumen 220 has a volume generally in the range from about 25 to 280 nL, and more typically in the range from about 25 to 160 nL. Unlike micro-needle 100 of FIG. 1, the entirety of its length is hollow. Micro-needle 200 may have the same or similar length and diameter dimensions as discussed above, but may instead have smaller dimensions as the electrochemical cell is located outside micro-needle lumen 220 rather than housed within it.

An electrochemical cell, defined by parallel, planar electrodes 208 and 212, is positioned at proximal end 205 of micro-needle 200. As such, the electrochemical cell remains outside the skin surface upon insertion of micro-needle into the skin of a patient. Electrode 208 defines a surface which circumferentially extends from proximal end 205 of micro-needle 200. Here, electrode 208 is in the form of an annular ring, as shown in FIG. 2B but may have any suitable shape, such as square or rectangular. Electrode 212 is spaced proximally from electrode 208, defining a spacing there between which functions as the reaction zone 210 of the electrochemical cell. This spacing is generally in the range from about 50 to 80 μm, and typically does not exceed 150 μm. Electrode 212 preferably has a shape and size that correspond to the shape and size of electrode 208. Here, electrode 212 preferably has a circular disk shape and a diameter the same as the outer diameter of electrode 208. This diameter dimension is generally in the range from about 600 to 800 μm, and typically does not exceed 1 mm. The inner diameter of electrode 108 preferably matches the diameter of outer plating 214, and thus has values mentioned above.

At least the surfaces of the electrodes of FIGS. 1 and 2 that face the reaction zones 110 and 210 within micro-needles 100 and 200, respectively, are comprised of highly conductive metal, such as palladium, gold, platinum, silver, iridium, carbon, doped indium tin oxide, stainless steel and the like, or a combination of such materials. Most typically the metal is gold, platinum or palladium. Although the entire electrode may be made of metal, each electrode can be made up of an inert support or backing substrate on the surface of which is a thin layer of the metal component (e.g., an electroplated metal layer) of the electrode.

Hydrophilic Gel Material

The constituent transfer medium of the sampling means of the present invention may occupy the entire volume of the reaction zones 110 and 210, respectively, and at least a portion of each micro-needle needle lumen 120 and 220, respectively, but may completely fill the lumen. The constituent transfer medium is preferably made of a water-based gel material or matrix having a high affinity for water, i.e., is highly water-absorbent. The hydrophilic gel helps to precondition the electrodes and reconstitute the reagent material in preparation for the electrochemical measurement of target analytes.

The transfer medium's ability to absorb fluids, particularly water, is dependent upon the extent to which the transfer medium is saturated prior to being exposed to fluid. In order to reduce the time for which the micro-needle is inserted or applied to the skin, the constituent transfer medium is preferably provided in a fully saturated state prior to insertion of the micro-needle into the skin. As such, only the non-fluid constituents, including the one or more targeted constituents, contained within the biological fluid are transferred, thereby eliminating time for the preliminary transfer of biological fluid. As interstitial fluid, for example, is about 98% water, the reduction in diffusion time through the gel may be significant in certain applications.

As between the constituents which are able to diffuse into and through the gel matrix, the speed at which they reach the reaction zone will vary depending on the size of the molecules of the constituents. Generally, the smaller the molecule the faster the diffusion rate through the gel. As many commonly targeted analytes, such as glucose, electrolytes, ascorbic acid, uric acid, etc., have small molecules, these analytes will diffuse through the gel matrix faster than other components of the interstitial fluid comprised of larger molecules.

Figure 3:
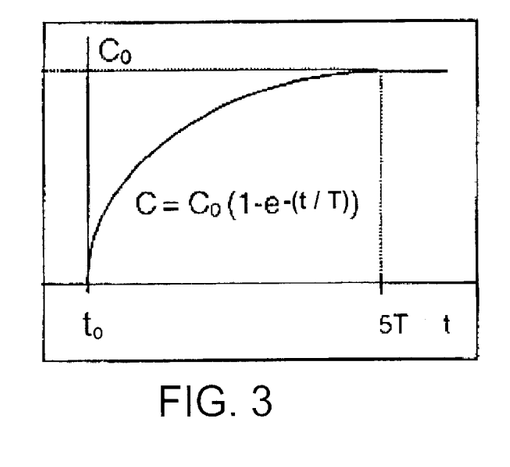
FIG. 3 is a graphical representation of the first order system of the gel matrix of the present invention.

The concentration kinetics of the selected hydrogel is that of a first order system. As such, the constituent transfer rate and the analyte concentration level of the biological fluid are more predictable. This first order system is represented by the following equation and the graph of FIG. 3:

$$C = C_o(1 - e^{-(t/T)})$$

where C is the concentration of the analyte within the gel material, $C_o$ is the concentration of the analyte in the interstitial fluid t is the time at which the measurement is made, and T is time constant of the system. The value of the time constant depends on several factors: (1) the area of the interface between the hydrogel and the interstitial fluid (i.e., the surface area of the opening defined by edge 116 and 216 of micro-needles 100 and 200, respectively, (2) the volume of the hydrogel, and (3) the transport characteristics of the target analyte through the particular hydrogel material used.

The graph of FIG. 3 depicts the first order system described in the above equation. The dependent axis represents time (t) where $t_o$ is the point in time at which a micro-needle is inserted into the skin. With hydrogel materials suitable for use with the present invention, the time it takes for the constituent concentration in the hydrogel to reach equilibrium with that of the biological fluid present at the distal opening of the micro-needle, is generally no more than about 5 times the time constant of the system. If the time to achieve equilibrium is impractical for a given application, the micro-needle may be removed from the skin prior to reaching equilibrium and then the analyte concentration level within the patient ($C_o$) can be calculated based on the first order characteristics of the system. Alternately, the time duration of contact between the micro-needle and the interstitial fluid may be controlled (i.e., fixed) and $C_o$ can be derived based on the first order equation above.

Gel materials suitable for use as the constituent transfer medium of the present invention include natural gels made up of naturally occurring polymers, such as agarose, gelatin, mucopolysaccharide, starch and the like, and synthetic gels made up, at least in part, of synthetic polymers, such as anyone of the neutral water-soluble polymers or polyelectrolytes (i.e., synthetic or natural polymers which form ionic charges when dissolved in water), such as polyvinyl pyrrolidone, polyethylene glycol, polyacrylic acid, polyvinyl alcohol, polyacrylamide, and copolymers thereof.

Reagents

In order to single out and sense the target analyte or constituent selected for analysis over the other constituents in the sampled biological fluid, a redox reagent is typically employed within the reaction zone within the electrochemical cell. The redox reagent material is typically deposited on at least one of the facing surfaces of the two electrodes whereby biological fluid present in the reaction zone chemically reacts with the reagent material. As such, the reagent is preferably coated or deposited on the surface(s) by means of dip coating. The reagent being used is selected based on the analyte targeted for detection. The interaction of the reagent system and the corresponding constituent or analyte is employed in the electrochemical measurement protocol to determine the concentration of the target analyte or constituent in the cell.

The reagent system present in the reaction area typically includes at least an enzyme(s) and a mediator. In many embodiments, the enzyme member(s) of the reagent system is an enzyme or a plurality of enzymes that work in concert to oxidize the analyte of interest. In other words, the enzyme component of the reagent system is made up of a single analyte oxidizing enzyme or a collection of two or more enzymes that work in concert to oxidize the analyte of interest. Enzymes of interest include oxidases, dehydrogenases, lipases, kinases, diaphorases, quinoproteins and the like. The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the reagent system is a glucose-oxidizing enzyme (e.g., a glucose oxidase or glucose dehydrogenase).

The second component of the reagent system is a mediator component, which is made up of one or more mediator agents. A variety of different mediator agents are known in the art and include: ferricyanide, phenazine ethosulphate, phenazine methosulfate, pheylenediamine, 1-methoxyphenazine methosulfate, 2,6-dimethyl-1,4-benzoquinone, 2,5-dichloro-1,4-benzoquinone, ferrocene derivatives, osmium bipyridyl complexes, ruthenium complexes and the like. In those embodiments where glucose is the analyte of interest and either glucose oxidase or glucose dehydrogenase is the enzyme component, the mediator of particular interest is ferricyanide. Other reagents that may be present in the reaction area include buffering agents, (e.g., citraconate, citrate, phosphate), "Good" buffers and the like.

The reagent is generally present in dry form. The amounts of the various components may vary wherein the amount of enzyme component typically ranges from about 0.1 to 10% by weight.

The Sensor System

In the sensor systems of the present invention, the reference and working electrodes of the electrochemical cell are in electrical communication with a control means that sets the input reference signal transmitted to the electrochemical cell, receives the output signal from the electrochemical cell and then derives the concentration level of the analyte within the sample from the output signal. In other words the control means provides a means for applying an electrical current between the two electrodes, measuring a change in the current over time and relating the observed change in current to the concentration of analyte present in the electrochemical cell. The concentration of the analyte in the patient's blood is then derived, the numerical value of which is preferably provided as an output signal to a display means.

Figure 4:
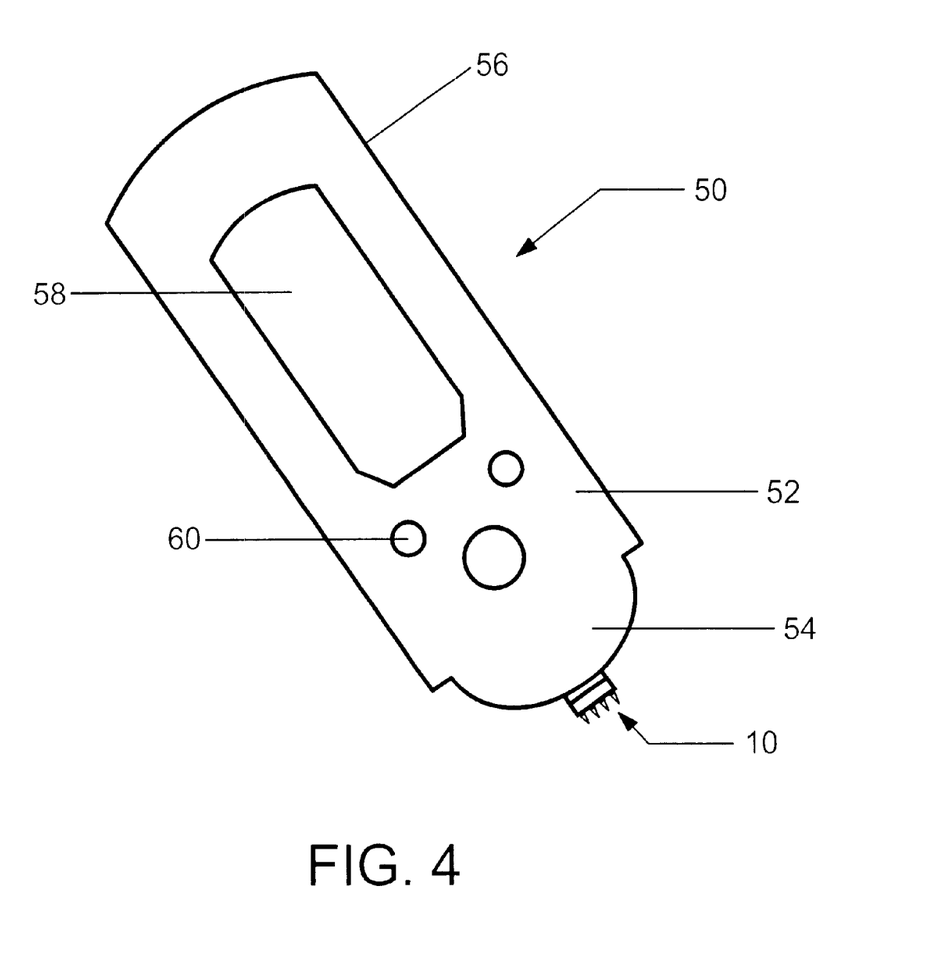
FIG. 4 is a schematic representation of the sampling and measurement device of the present invention.

Preferably, the control and display means are integrally housed within a hand-held control unit such as that illustrated in FIG. 4. The control unit preferably also provides a means of securing or holding one or more micro-needles or an array of micro-needles in a position and arrangement suitable for the particular sampling and measuring application at hand.

Referring now to FIG. 4, there is shown a schematic representation of a sensor system 50 of the subject invention. Sensor system 50 comprises a hand-held control unit 52 and a sensor device 10 operatively mounted to distal end 54 of control unit 52. Sensor device 10 includes array of the micro-needles of the present invention, such as micro-needle 100 of FIGS. 1 and 2. Control unit 52 has a housing 56, preferably made of a medical grade plastic material, having a low-profile configuration which houses a means (not shown) for controlling the measurement means of sensor device 10, i.e., generating and transmitting input reference signals to the electrochemical cell of micro-needle 100 and receiving output measurement signals from the cell. A software algorithm programmed within control unit 52 automatically calculates and determines the concentration of the target analyte in the biological sample upon receipt of the output signal. The concentration level (among other desired information) is then transmitted to an external display means or screen 58 that displays information to the user. Control interface buttons 60 are provided to allow the user to input information, such as the type of analyte targeted for measurement, to the control means.

Sensor device 10 is electrically and physically coupled to control unit 52. Electrical communication between the two is established by means of conductive contacts (not shown) on device 10 and corresponding electrical traces (not shown) within control unit 52. Preferably, device 10 and control unit 52 are physically coupled by a quick lock-and-release mechanism (many of which are commonly known) such that a used sensor device can be easily removed and replaced. Control unit 52 is preferably reusable and usable with any number of sensor devices of the subject invention. These features facilitate the taking of multiple samples and measurements in an efficient and rapid manner.

Methods of Use

Also provided by the subject invention are methods for using the subject devices and sensor systems to determine the concentration of an analyte in a physiological sample. A variety of different analytes may be detected using the subject sensor systems, where representative analytes include glucose, cholesterol, lactate, alcohol, and the like.

In practicing the subject methods (with reference to the Figures), the first step is to provide a sensor device 10 having one or more micro-needles 100 of the present invention. Preferably, sensor device 10 is particularly configured (i.e., containing the appropriate reagent) for targeting the analyte (s) of interest. The sensor device 10 is operatively engaged and interfaced with a control unit 52 that can be manually held and controlled by the user. Control unit 52 is programmed for testing the targeted analyte(s). The user positions sensor device 10 over a selected area of the patient's skin, and, with slight pressure, the array of micro-needles 100 of sensor device 10 are caused to penetrate into the skin. The depth to which the micro-needles 100 are inserted will depend on the length of the respective micro-needles or by some other means associated with the sensor unit 10 for limiting the insertion depth.

Upon insertion into the patient's skin, an amount (i.e., a sample) of constituents of the biological fluid present at the open tips 102 of micro-needles 100 is absorbed by the gel-based, constituent transfer medium into lumens 120 of the respective micro-needles by means of osmosis. Once in the reaction zone, the targeted analyte(s) chemically reacts with the selected reagent(s) to form electroactive products. The electroactive products are then either oxidized or reduced by the optional mediator or directly by the working electrode 108. The resulting output signal level is then conducted to the control unit by electrode 108. A software algorithm programmed within control unit 52 then automatically determines the differential between the output and reference signals, derives the concentration of analyte in the sample from this differential value, and then derives the corresponding concentration level of the selected analyte(s) in the patient's blood. Any or all of these values may be displayed by display means or screen 58.

A device such as control unit 52 which automatically calculates and determines the concentration of a selected analyte in a biological sample and/or in the patient's system, such that a user need only insert a micro-needle of the subject invention into the patient's skin and then read the final analyte concentration result from a display of the device, is further described in U.S. Pat. No. 6,193,873 entitled "Sample Detection to Initiate Timing of an Electrochemical Assay," the disclosure of which is herein incorporated by reference.

Kits

Also provided by the subject invention are kits for use in practicing the subject methods. The kits of the subject invention include at least one subject sensor device having one or more micro-needles. The kits may also include a reusable or disposable control unit that may be used with reusable or disposable sensor devices of the kit or from other kits of the subject invention. These kits may include sensors having an array of micro-needles having the same or different lengths. Certain kits may include various sensors each containing the same or different reagents. Also, more than one reagent may be provided within a single micro-needle array, wherein one or more of the micro-needles are provided with a first reagent for testing a first target analyte and one or more other micro-needles are provided with other reagents for testing other targeted analytes. Finally, the kits preferably include instructions for using the subject sensors in the determination of an analyte concentration in a physiological sample. These instructions may be present on one or more of the packaging, a label insert, or containers present in the kits, and the like.

It is evident from the above description that the subject inventions are easy to use and can provide for analyte testing without the need to cut or lance the skin and without minimal or no pain and blood. As such, the subject invention represents a significant contribution to the field.

The subject invention is shown and described herein in what is considered to be the most practical, and preferred embodiments. It is recognized, however, that departures may be made there from, which are within the scope of the invention, and that obvious modifications will occur to one skilled in the art upon reading this disclosure.

Although the present invention is useful for many applications, the sampling of various biological fluids and the detection of many types of constituents, the invention has been described primarily in the context of the detection of analytes in interstitial fluids, and as being particularly useful for the detection of glucose in interstitial fluid. Thus, the specific devices and methods disclosed and the applications, biological fluids and constituents discussed herein are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A system for sampling biological fluid constituents from the skin of a patient and measuring a target constituent within the biological fluid, the system comprising:
   (a) a micro-needle at least a portion of which is hollow and having an open distal end for accessing the biological fluid;
   (b) an electrochemical cell associated with the micro-needle, the cell comprising an outer electrode and an inner electrode wherein the electrodes each have a cylindrical configuration and are spaced from each other in a co-axial relationship, the micro-needle formed at least partially by the outer electrode;
   (c) a water-absorbent gel matrix at least partially contained within the hollow portion of the micro-needle and the space between the electrodes; and
   (d) a control unit in electrical communication with the electrochemical cell for measuring the concentration of the target constituent of the biological fluid.

2. The system according to claim 1 further comprising a display unit in electrical communication with the control unit for displaying information related to the measuring of the target constituent.

3. The system according to claim 1 further comprising a housing and a support means wherein the control unit is housed within the housing and the micro-needle is mounted to the support means.

4. The system of claim 1 wherein the gel matrix comprises a natural gel.

5. The system of claim 4 wherein the natural gel is selected from the group comprising agarose, gelatin, mucopolysaccharide and starch.

6. The system of claim 1 wherein the gel matrix comprises a synthetic gel.

7. The system of claim 6 wherein the synthetic gel comprises a neutral water-soluble polymer.

8. The system of claim 1 wherein the electrochemical cell is adjacent to a proximal end of the micro-needle.

9. The system of claim 1 comprising an array of micro-needles.

10. The system of claim 1 wherein the outer electrode is a reference electrode and the inner electrode is a working electrode, and further wherein the control unit comprises:

means for sending an electrical reference signal to the reference electrode and for receiving an electrical output signal from the working electrode; and means for automatically determining the concentration of the target constituent in the biological fluid upon receipt of the electrical output signal.

11. The system of claim 1 wherein the outer electrode and the inner electrode have substantially the same length.

12. The system of claim 1 wherein the outer electrode is longer than the inner electrode.

* * * * *